US012714602B2

(12) United States Patent
Lemonis

(10) Patent No.: US 12,714,602 B2
(45) Date of Patent: Aug. 25, 2026

(54) GENERATING A REFRACTIVE OPHTHALMIC NOMOGRAM

(71) Applicant: Alcon Inc., Fribourg (CH)

(72) Inventor: Sissimos Lemonis, Rückersdorf (DE)

(73) Assignee: Alcon Inc., Fribourg (CH)

( * ) Notice: Subject to any disclaimer, the term of this patent is extended or adjusted under 35 U.S.C. 154(b) by 632 days.

(21) Appl. No.: 18/302,356

(22) Filed: Apr. 18, 2023

(65) Prior Publication Data

US 2023/0355440 A1 Nov. 9, 2023

Related U.S. Application Data

(60) Provisional application No. 63/364,114, filed on May 4, 2022.

(51) Int. Cl.
*A61F 9/008* (2006.01)
*G16H 20/40* (2018.01)

(52) U.S. Cl.
CPC ............ *A61F 9/008* (2013.01); *G16H 20/40* (2018.01); *A61F 2009/00859* (2013.01); *A61F 2009/00872* (2013.01)

(58) Field of Classification Search
CPC .. A61F 9/008; A61F 9/00804; A61F 9/00827; A61F 2009/00859; A61F 2009/00872; A61F 2009/00897
USPC ........................................................ 606/10
See application file for complete search history.

(56) References Cited

U.S. PATENT DOCUMENTS 6,467,906 B1 10/2002 Alpins
8,273,077 B2 9/2012 Macrae et al.
8,409,178 B2 4/2013 Dai et al.
9,931,199 B2 * 4/2018 Albertazzi .............. A61F 9/007
11,246,664 B2 * 2/2022 Andrews ............... A61F 2/1662
2005/0107775 A1 * 5/2005 Huang ............... G02B 26/0816 606/5
2008/0306573 A1 * 12/2008 Campin .................. A61F 9/008 607/89
2016/0038276 A1 2/2016 Albertazzi
2019/0365568 A1 * 12/2019 Riedel ................. A61F 9/00827
(Continued)

FOREIGN PATENT DOCUMENTS

EP 3065680 B1 5/2018
WO WO-2019229696 A1 * 12/2019 ......... A61F 9/00827
WO 2021173843 A1 9/2021

*Primary Examiner* — Ahmed M Farah

(57) ABSTRACT

A system for generating an ophthalmic nomogram for treating an eye includes a computer. The computer stores post-operation refraction data. The post-operation refraction data comprises notations that comprise a sphere and a cylinder and describe a post-operation correction. The computer creates a nomogram data set comprising selected spheres by performing the following for each notation: if the notation is expressed as a plus notation, determine a minus notation corresponding to the plus notation; if the notation is expressed as a minus notation, determine a plus notation corresponding to the minus notation; identify whether the plus notation or the minus notation has a lower absolute sphere; designate the lower absolute sphere of the identified notation as a candidate sphere; and determine whether to designate the candidate sphere as a selected sphere. The computer program calculates the ophthalmic nomogram from the selected spheres.

21 Claims, 5 Drawing Sheets

(56) References Cited

U.S. PATENT DOCUMENTS

| | | | | |
|---|---|---|---|---|
| 2020/0261264 | A1 | 8/2020 | Lobanoff | |
| 2023/0404804 | A1 * | 12/2023 | Riedel | A61F 9/008 |

* cited by examiner

GENERATING A REFRACTIVE OPHTHALMIC NOMOGRAM

TECHNICAL FIELD

The present disclosure relates generally to ophthalmic laser surgical systems, and more particularly to generating a refractive ophthalmic nomogram.

BACKGROUND

Refractive error-correcting ophthalmic surgical procedures, such as corneal and intraocular procedures, use a variety of techniques to correct refractive error. For example, a laser can be used to reshape the cornea, an intraocular lens can be inserted into the eye and may even replace the crystalline lens, or a lenticle can be extracted from or inserted into the corneal stroma to correct refractive error. In practice, the results of real-world surgery deviate from the perfect laboratory environment because of subtle differences among, e.g., laser systems, intraocular lenses, ablation designs, formulas used to calculate treatments, surgeons, patients, and operating room environments. The differences may be compensated for using a refractive nomogram, which can be calculated for a particular refractive correction system. The nomogram is generated by analyzing data from previous operations performed by the system to determine relationships between the desired target corrections and actual post-operation corrections.

BRIEF SUMMARY

In certain embodiments, a system for generating an ophthalmic nomogram for treating an eye includes a computer. The computer includes memory and logic. The memory stores a computer program and post-operation refraction data for generating the ophthalmic nomogram. The post-operation refraction data comprises notations. Each notation comprising a sphere and a cylinder and describes a post-operation correction associated with a target correction. The target correction has a target sphere. The logic executes the computer program to create a nomogram data set comprising selected spheres. The logic executes the computer program that: performs the following for each notation to yield the selected spheres: if the notation is expressed as a plus notation, determine a minus notation corresponding to the plus notation; if the notation is expressed as a minus notation, determine a plus notation corresponding to the minus notation; identify whether the plus notation or the minus notation has a lower absolute sphere; designate the lower absolute sphere of the identified notation as a candidate sphere; and determine whether to designate the candidate sphere as a selected sphere. The computer program calculates the ophthalmic nomogram from the selected spheres.

Embodiments may include none, one, some, or all of the following features: The logic determines whether to designate the candidate sphere as a selected sphere by, if an absolute cylinder of the notation is equal to two times an absolute sphere of the notation, determining whether to include or exclude the candidate sphere from the selected spheres. The logic determines whether to designate the candidate sphere as a selected sphere by, if an absolute cylinder of the notation is not equal to two times an absolute sphere of the notation, determining whether the notation describes a mixed astigmatism. The logic determines whether to designate the candidate sphere as a selected sphere by, if the notation describes a mixed astigmatism, determining whether to include or exclude the candidate sphere. The logic determines that an absolute cylinder of the notation is equal to two times an absolute sphere of the notation, and performs a distribution procedure to distribute plus notations and minus notations of the selected spheres. The logic may perform the distribution procedure by: if a sphere of a previous iteration was from the minus notation, selecting the sphere of the plus notation; and if the sphere of the previous iteration was from the plus notation, selecting the sphere of the minus notation. The logic may perform the distribution procedure by randomly selecting the sphere of either the plus notation or the minus notation as the selected sphere. The logic calculates the ophthalmic nomogram from the selected spheres by performing the following for each selected sphere of the nomogram data set: determining a post-operation correction corresponding to a selected sphere; and identifying the target sphere of the target correction associated with the post-operation correction. The logic creates a graph of the post-operation spheres versus the target spheres. The logic may create the graph of the post-operation spheres versus the target spheres by performing a regression analysis of the post-operation spheres versus the target spheres in order to determine a line that describes a relationship between the post-operation spheres and the target spheres. The logic may create the graph of the post-operation spheres versus the target spheres by: performing a first regression analysis for a first diopter range of the post-operation spheres versus the target spheres to determine a first line that describes a relationship between the post-operation spheres and the target spheres in the first diopter range; and performing a second regression analysis for a second diopter range of the post-operation spheres versus the target spheres to determine a second line that describes a relationship between the post-operation spheres and the target spheres in the second diopter range. The logic calculates the ophthalmic nomogram from the selected spheres by identifying a subset of the selected spheres corresponding to a class of patients, and calculating the ophthalmic nomogram from the subset of the selected spheres. The logic plans a treatment for the eye according to the ophthalmic nomogram. The system may include a laser device that performs the treatment for the eye.

In certain embodiments, a method for generating an ophthalmic nomogram for treating an eye includes storing, by a computer, a computer program and post-operation refraction data for generating the ophthalmic nomogram. The post-operation refraction data comprises notations. Each notation comprising a sphere and a cylinder and describes a post-operation correction associated with a target correction. The target correction has a target sphere. The method includes executing, by the computer, the computer program to create a nomogram data set comprising selected spheres. The computer executing the computer program includes performing the following for each notation to yield selected spheres: if the notation is expressed as a plus notation, determining a minus notation corresponding to the plus notation; if the notation is expressed as a minus notation, determining a plus notation corresponding to the minus notation; identifying whether the plus notation or the minus notation has a lower absolute sphere; designating the lower absolute sphere of the identified notation as a candidate sphere; and determining whether to designate the candidate sphere as a selected sphere. The computer executing the computer program includes calculating the ophthalmic nomogram from the selected spheres.

Embodiments may include none, one, some, or all of the following features: Determining whether to designate the candidate sphere as a selected sphere includes, if an absolute cylinder of the notation is equal to two times an absolute sphere of the notation, determining whether to include or exclude the candidate sphere from the selected spheres. Determining whether to designate the candidate sphere as a selected sphere includes, if an absolute cylinder of the notation is not equal to two times an absolute sphere of the notation, determining whether the notation describes a mixed astigmatism. Determining whether to designate the candidate sphere as a selected sphere includes, if the notation describes a mixed astigmatism, determining whether to include or exclude the candidate sphere. The method includes determining that an absolute cylinder of the notation is equal to two times an absolute sphere of the notation, and performing a distribution procedure to distribute plus notations and minus notations of the selected spheres. Calculating the ophthalmic nomogram from the selected spheres includes performing the following for each selected sphere of the nomogram data set: determining a post-operation correction corresponding to a selected sphere; and identifying the target sphere of the target correction associated with the post-operation correction. Calculating the ophthalmic nomogram also includes creating a graph of the post-operation spheres versus the target spheres. The method includes planning a treatment for the eye according to the ophthalmic nomogram.

In certain embodiments, a system for generating an ophthalmic nomogram for treating an eye includes a computer. The computer includes memory and logic. The memory stores a computer program and post-operation refraction data for generating the ophthalmic nomogram. The post-operation refraction data comprises notations. Each notation comprising a sphere and a cylinder and describes a post-operation correction associated with a target correction. The target correction has a target sphere. The logic executes the computer program to create a nomogram data set comprising selected spheres. The logic executes the computer program that: performs the following for each notation to yield the selected spheres: if the notation is expressed as a plus notation, determine a minus notation corresponding to the plus notation; if the notation is expressed as a minus notation, determine a plus notation corresponding to the minus notation; identify whether the plus notation or the minus notation has a lower absolute sphere; designate the lower absolute sphere of the identified notation as a candidate sphere; and determine whether to designate the candidate sphere as a selected sphere. The logic determines whether to designate the candidate sphere as a selected sphere by: if an absolute cylinder of the notation is equal to two times an absolute sphere of the notation, determining whether to include or exclude the candidate sphere from the selected spheres; if an absolute cylinder of the notation is not equal to two times an absolute sphere of the notation, determining whether the notation describes a mixed astigmatism; and if the notation describes a mixed astigmatism, determining whether to include or exclude the candidate sphere. The logic determines that an absolute cylinder of the notation is equal to two times an absolute sphere of the notation, and performs a distribution procedure to distribute plus notations and minus notations of the selected spheres. The logic performs the distribution procedure by: if a sphere of a previous iteration was from the minus notation, selecting the sphere of the plus notation, and if the sphere of the previous iteration was from the plus notation, selecting the sphere of the minus notation; or randomly selecting the sphere of either the plus notation or the minus notation as the selected sphere. The logic calculates the ophthalmic nomogram from the selected spheres by performing the following for each selected sphere of the nomogram data set: determining a post-operation correction corresponding to a selected sphere; and identifying the target sphere of the target correction associated with the post-operation correction. The logic creates a graph of the post-operation spheres versus the target spheres. The logic may create the graph of the post-operation spheres versus the target spheres by performing a regression analysis of the post-operation spheres versus the target spheres in order to determine a line that describes a relationship between the post-operation spheres and the target spheres. The logic may create the graph of the post-operation spheres versus the target spheres by: performing a first regression analysis for a first diopter range of the post-operation spheres versus the target spheres to determine a first line that describes a relationship between the post-operation spheres and the target spheres in the first diopter range; and performing a second regression analysis for a second diopter range of the post-operation spheres versus the target spheres to determine a second line that describes a relationship between the post-operation spheres and the target spheres in the second diopter range. The logic calculates the ophthalmic nomogram from the selected spheres by identifying a subset of the selected spheres corresponding to a class of patients, and calculating the ophthalmic nomogram from the subset of the selected spheres. The logic plans a treatment for the eye according to the ophthalmic nomogram. The system includes a laser device that performs the treatment for the eye.

DESCRIPTION OF EXAMPLE EMBODIMENTS

Figure 1:
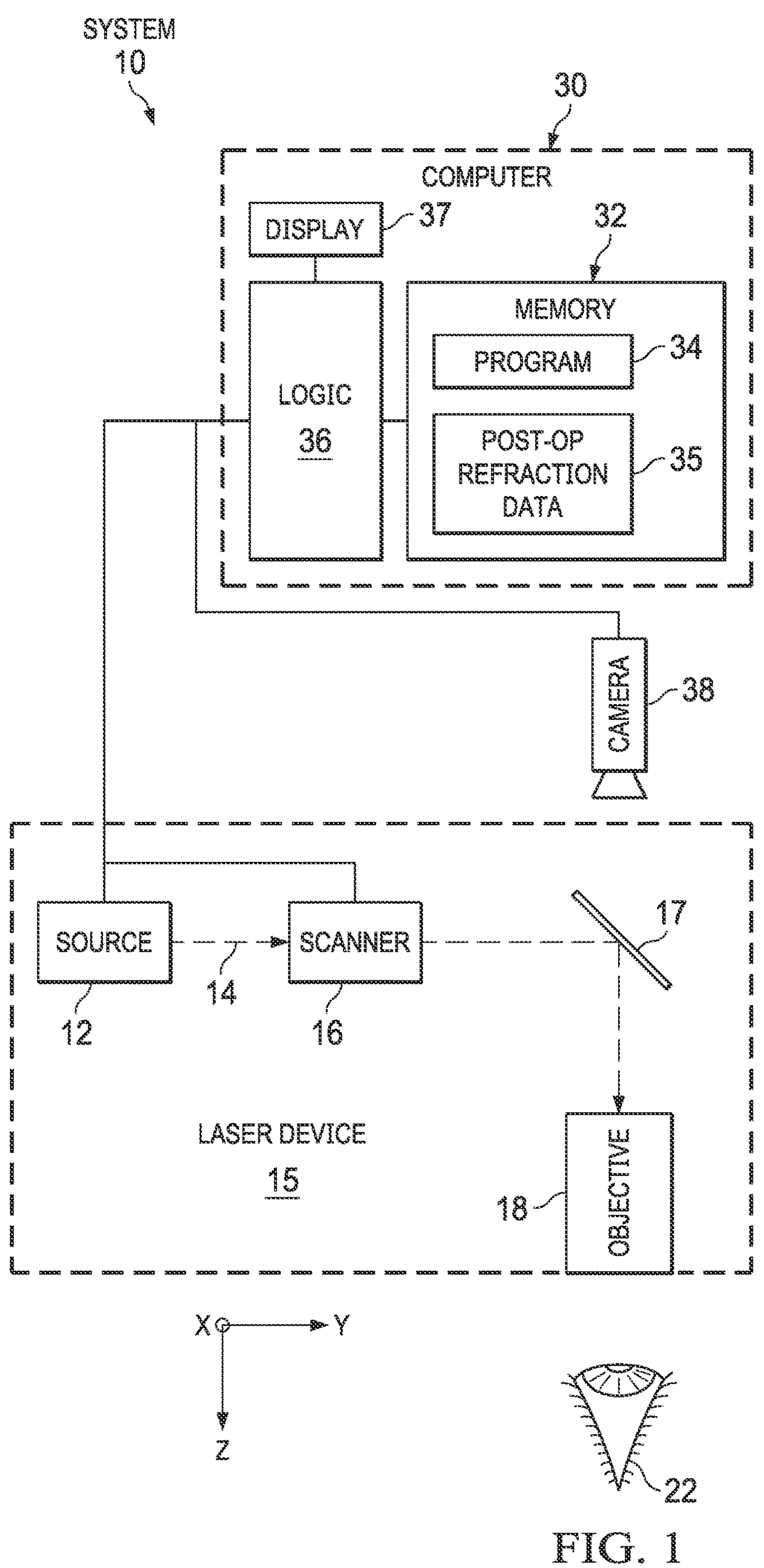
FIG. 1 illustrates an example of an ophthalmic laser system that performs refractive treatment on an eye, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

As an overview, refractive notation, expressed as a plus or minus notation, is used to describe target refractive corrections and their resulting post-operation corrections. A nomogram is used to reduce the difference between the target and post-operation corrections. However, a user's preference for a plus or a minus notation can skew the nomogram. Moreover, the refractive notation for mixed astigmatism can misdescribe the correction, reducing the accuracy of the nomogram. Accordingly, embodiments of the invention analyze data from astigmatism cases in order to compensate for these problems.

In more detail, when calculating a nomogram, target corrections are compared to post-operation corrections. A target correction is the refractive correction the procedure is set to perform (e.g., the correction a laser device is instructed to perform), typically in response to instructions from a user such as a surgeon. A post-operation (or achieved) correction is the actual refractive correction resulting from the procedure.

Refractive notation describes the refractive correction. In general, a refractive notation comprises a sphere, cylinder, and axis. Sphere describes the spherical correction (for myopia or hyperopia), which is equal across all meridians of the eye. The value of the sphere indicates the amount of lens power prescribed to correct the myopia or hyperopia. Cylinder and axis describe how the correction for astigmatism differs from the spherical correction. Astigmatism occurs when the cornea is not perfectly spherical such that light rays converge to more than one focal point. The axis indicates the meridian of the astigmatism correction, and the cylinder represents the amount of correction. For astigmatism, the positive/negative power and its related axis can be displayed interchangeably.

Some users have a preferred cylinder notation, e.g., plus or minus cylinder notation, that they use more than the other. Preferring the plus or the minus cylinder notation, however, can misdescribe astigmatism corrections as over-correction or under-correction of the sphere. Moreover, refractive notation for mixed astigmatism misdescribes the correction. Mixed astigmatism occurs when light rays converge at one focal point in front of the retina and another behind the retina. In general, mixed astigmatism requires no spherical correction, only cylindrical correction for axes separated by 90°. However, the refractive notation for mixed astigmatism includes non-zero spherical components, which misleadingly indicates there is a spherical correction. Accordingly, the embodiments described herein analyze astigmatism cases in order to reduce the spurious effects of user preferences and mixed astigmatism notation on nomograms.

FIG. 1 illustrates an example of an ophthalmic laser system 10 that performs an ophthalmic treatment on an eye 22, according to certain embodiments. The ophthalmic treatment may be any suitable refractive correction surgery, such as laser refractive surgery (e.g., laser ablation or photodisruption surgery), cataract surgery (e.g., intraocular lens surgery), or other surgery for refractive correction. In laser refractive surgery, a laser can ablate the cornea to reshape the cornea, or a laser can cause photodisruptions in the cornea to, e.g., create changes in the shape of the cornea, create a pocket to insert an implant, or create a lenticule to extract. In cataract surgery, an intraocular lens can be inserted into the eye and may even replace the crystalline lens.

In the illustrated example, system 10 includes a laser device 15, a camera 38, and a control computer 30, coupled as shown. Laser device 15 includes controllable components, such as a laser source 12, a scanner 16, one or more optical elements 17, and/or a focusing objective 18, coupled as shown. Computer 30 includes logic 36, a memory 32 (which stores a computer program 34 and post-operation refractive data 35), and a display 37, coupled as shown. Any suitable xyz-coordinate system may be used. For example, the z-direction may be defined by an axis (e.g., visual or optical) of the eye or the direction of laser beam propagation, and the xy-plane is orthogonal to the z-direction.

Turning to the parts of system 10, laser source 12 generates a laser beam comprising laser pulses that ablate, photocoagulate, photovaporize, photodisrupt, radiate, or otherwise interact with the tissue of eye 22. Laser source 12 may be an excimer, femtosecond, or other suitable laser, and may emit a laser beam with any suitable wavelength (e.g., infrared or ultraviolet). A laser shot list defines x and y coordinates of locations at which laser pulses are to be directed and the order in which the pulses are to be directed to perform the refractive treatment.

Scanner 16 directs the focal point of the laser beam in the x, y, and/or z-directions. Scanner 16 may direct the laser beam in any suitable manner. For example, scanner 16 may include a pair of galvanometrically-actuated scanner mirrors that can be tilted about mutually perpendicular axes. As another example, scanner 16 may include an electro-optical crystal that can electro-optically steer the laser beam. As another example, scanner 16 may include a deformable mirror that can direct the beam in a particular direction.

One (or more) optical elements 17 direct the laser beam towards focusing objective 18. An optical element 17 can act on (e.g., transmit, reflect, refract, diffract, collimate, condition, shape, focus, modulate, and/or otherwise act on) a laser beam. Examples of optical elements include a lens, prism, mirror, diffractive optical element (DOE), holographic optical element (HOE), and spatial light modulator (SLM). In the example, optical element 17 is a mirror. Focusing objective 18 focuses the focal point of laser beam towards a point of eye 22. In the example, focusing objective 18 is an objective lens.

Camera 38 records images of the eye 22. Examples of camera 38 include a video, an optical coherence tomography, or an eye-tracking camera. Camera 38 delivers image data, which represent recorded images of the eye 22, to computer 30. Computer 30 may carry out image processing on the image data to monitor treatment of eye 22. In certain embodiments, images recorded by camera 38 may be used to monitor the current application of pulses.

In certain embodiments, computer 30 executes computer program 34 to create a nomogram data set that includes refraction notation (spherical and astigmatism) selected to generate a nomogram. In the embodiments, post-operation refraction data 35 includes target corrections and their associated post-operation corrections. The corrections are expressed using a refractive notation that includes a sphere and cylinder, where "sphere" and "cylinder" refer to the spherical and cylindrical values, respectively, of a notation.

In the embodiments, computer 30 selects spheres to create the nomogram data set used to generate the nomogram. As an overview, computer 30 performs the following for each notation of data 35 to yield the selected spheres: perform the following for each notation of the plurality of notations to yield the plurality of selected spheres: if the notation is expressed as a plus notation, determine the minus notation corresponding to the plus notation; if the notation is expressed as a minus notation, determine the plus notation corresponding to the minus notation; identify whether the plus notation or the minus notation has a lower absolute value of the sphere ("absolute sphere"); designate the sphere of the identified notation (with the lower absolute sphere) as a candidate sphere; and perform further analysis to determine whether to designate the candidate sphere as the selected sphere, as described in more detail with respect to FIG. 3. Computer 30 and/or surgeon may plan the refractive treatment for the eye according to the ophthalmic nomogram. In certain embodiments, computer 30 performs other operations to create the nomogram data set, as described in more detail with respect to FIGS. 3 and 4.

In certain embodiments, computer 30 also controls components of system 10 in accordance with computer program 34. For example, computer 30 controls components (e.g., laser source 12, scanner 16, optical elements 17, and/or focusing objective 18) to focus the laser beam of laser device 15 at eye 22 according to a laser shot list to perform a refractive treatment. For example, computer 30 may instruct the laser device to perform the refractive treatment as planned according to the ophthalmic nomogram. In response, the laser device executes the refractive treatment.

Figure 2:
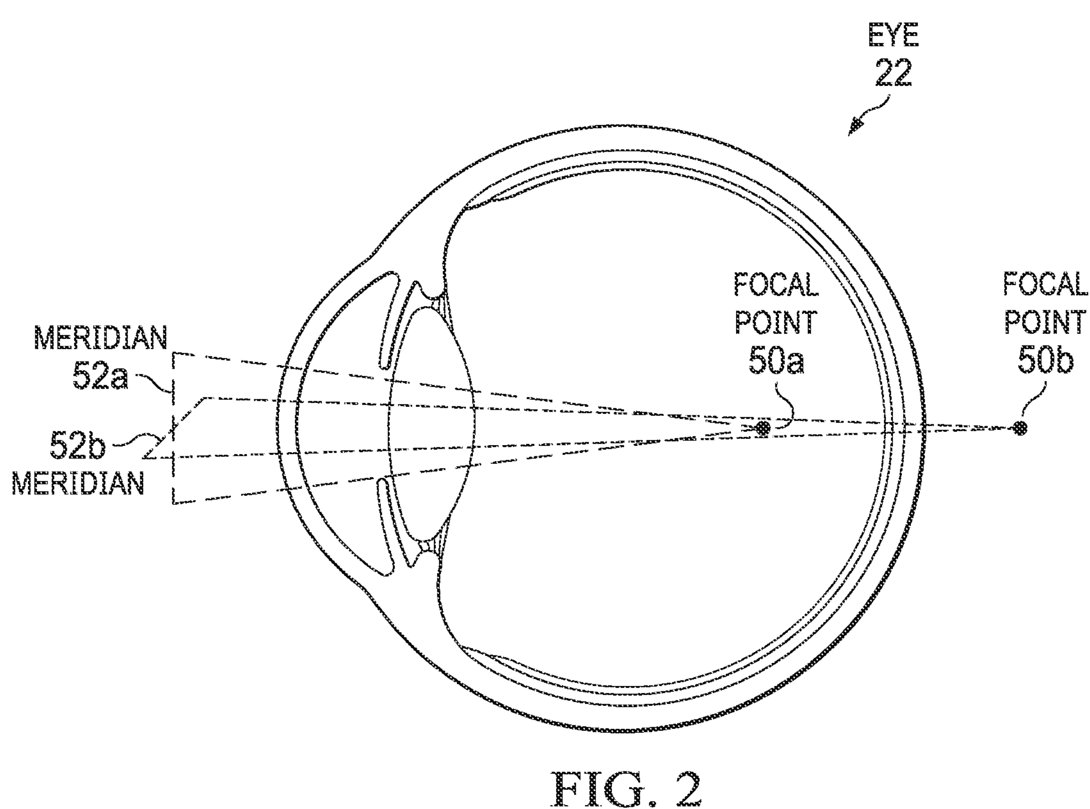
FIG. 2 illustrates an example of an eye with an astigmatism.

FIG. 2 illustrates an example of an eye 22 with mixed astigmatism. Astigmatism is a condition where the cornea is not perfectly spherical such that light rays converge to more than one focal point 50 (50_a_, 50_b_). Mixed astigmatism occurs when light rays converge at one focal point anterior to the retina 50_a_ and another 50_b_ posterior to the retina. Mixed astigmatism can be described using meridians 52 (52_a_, 52_b_). A meridian 52 is a line of longitude that intersects with the optical axis. In the example, the meridians 52_a_, 52_b_ (here shown separated from eye 22) are perpendicular to each other, but they need not be. Light along meridian 52_a_ converges at focal point 50_a_, and light along meridian 52_b_ converges at focal point 50_b_.

Refractive Notation. In general, refractive notation comprises a sphere, cylinder, and axis, e.g., −0.25 [sphere]−0.5 [cylinder]×90° [axis]. Sphere and cylinder refer to spherical and cylindrical values (typically in diopters), respectively, and axis refers to a meridian (typically in degrees). Sphere describes spherical correction (for myopia or hyperopia) that is equal across all meridians of the eye. The value of the sphere indicates the amount of lens power prescribed to correct the myopia or hyperopia. Cylinder and axis describe how the correction for astigmatism differs from the spherical correction. The axis indicates the meridian at which the astigmatism correction differs the least from the spherical correction, and the cylinder represents the difference.

The astigmatism correction may be expressed in plus cylinder and minus cylinder notations. In the plus cylinder notation, the cylinder value is the number of diopters more convergent than the sphere value. That is, the spherical component describes the most divergent meridian, and the cylindrical component describes the most convergent. In the minus cylinder notation, the cylinder value is the number of diopters more divergent than the sphere value. That is, the sphere component describes the most convergent meridian, and the cylinder component describes the most divergent.

The plus cylinder notation can be converted to the minus cylinder notation and vice versa. First, the cylindrical value and spherical value are algebraically added to get the new spherical value. Second, the sign of the cylindrical value is changed, plus to minus or vice versa. Third, the axis of the cylinder is rotated 90°. If the axis less than or equal to 90°, 90° is added to the axis. If the axis is greater than 90°, 90° is subtracted from the axis. In other words, to covert Notation1=S1+C1×axis1 to Notation2=S2+C2×axis2, the following are performed: S2=S1+C1, C2=−C1, and axis2=axis1+/−90°. As examples, −0.75+1.25×90° is converted to (or →)+0.5−1.25×180°; −0.25−0.5×90°→−0.75+0.5×180°; −1.0+0.75×90°→−0.25−0.75×180°; −0.75+1.25×180°→+0.5−1.25×90°; and −1.00+0.50×90°→−0.50−0.50×0°.

A nomogram may involve any suitable refractive notation or description, e.g., plus cylinder notation, minus cylinder notation, manifest refractive equivalent (MRSE), defocus equivalent index, cycloplegic measurement, or wavefront measurement. For example, the spherical equivalent (SEQ) may be used. The spherical equivalent is an estimate of refractive correction that essentially merges the spherical and cylindrical components. The spherical equivalent is calculated by adding the sum of the sphere value with half of the cylinder value. For example, given refractive notation −3.00+1.00×180°, the spherical equivalent is −3.00%/(+1.00)=−3.00+0.50=−2.50.

Astigmatism Notation and the Nomogram. Some users have a preferred cylinder notation, e.g., plus or minus cylinder notation, that they use more than the other. Preferring the plus or the minus cylinder notation, however, results in corrections of astigmatism misdescribed as over-correction or under-correction of the sphere. As an example, if a user prefers the plus cylinder notation of astigmatism, the refraction +1.00 −1.00×0° is interpreted as 1.00 D spherical over-correction (if myopia is the target correction), and the corresponding notation 0+1.00×90° represents astigmatism only with no spherical overcorrection. Moreover, the refraction −1.00+1.00 0° represents myopic under-correction, and the corresponding parent notation 0 −1.00×90° represents myopic cylinder with no spherical component. Furthermore, this example shows a limitation of the SEQ description. The SEQ is −0.50, even though this case is a pure astigmatism with no spherical component.

Moreover, refractive notation for mixed astigmatism misdescribes the correction. Overall, in the notation for mixed astigmatism, the absolute value of the cylinder ("absolute cylinder") is greater than the absolute value of the sphere ("absolute sphere"). For example, −0.75+1.25×180°→+0.5 −1.25×90° is an example of mixed astigmatism correction. In general, mixed astigmatism requires no spherical correction, only cylindrical correction. However, the notation that describes mixed astigmatism includes a non-zero spherical component, which misleadingly indicates a spherical correction. For example, mixed astigmatism notation −0.75+1.25×180°→+0.5 −1.25×90° includes spherical components −0.75 and +0.5, which typically indicate a spherical correction. However, this is not the case for a mixed astigmatism description. The first astigmatism portion includes the sphere of the first notation and the axis of the second notation, i.e., 0 −0.75×90°. The second astigmatism portion includes the sphere of the second notation and the axis of the first notation: 0+0.5×180° (or equivalently 0°). The resulting description is 0 −0.75×90°, 0+0.5×0°. Furthermore, to correct 0 −0.75×90°, the laser yields no change at the 90° region, but flattens the 180° (or 0°) region by −0.75 D. To correct 0+0.5×0°, the laser yields no change at the 0° region, but steepens the 90° region by +0.5 D. That is, the mixed astigmatism notation includes non-zero spherical components that do not ultimately describe a spherical correction. These misleading non-zero spherical components create spurious effects when used to generate a nomogram.

Figure 3A:
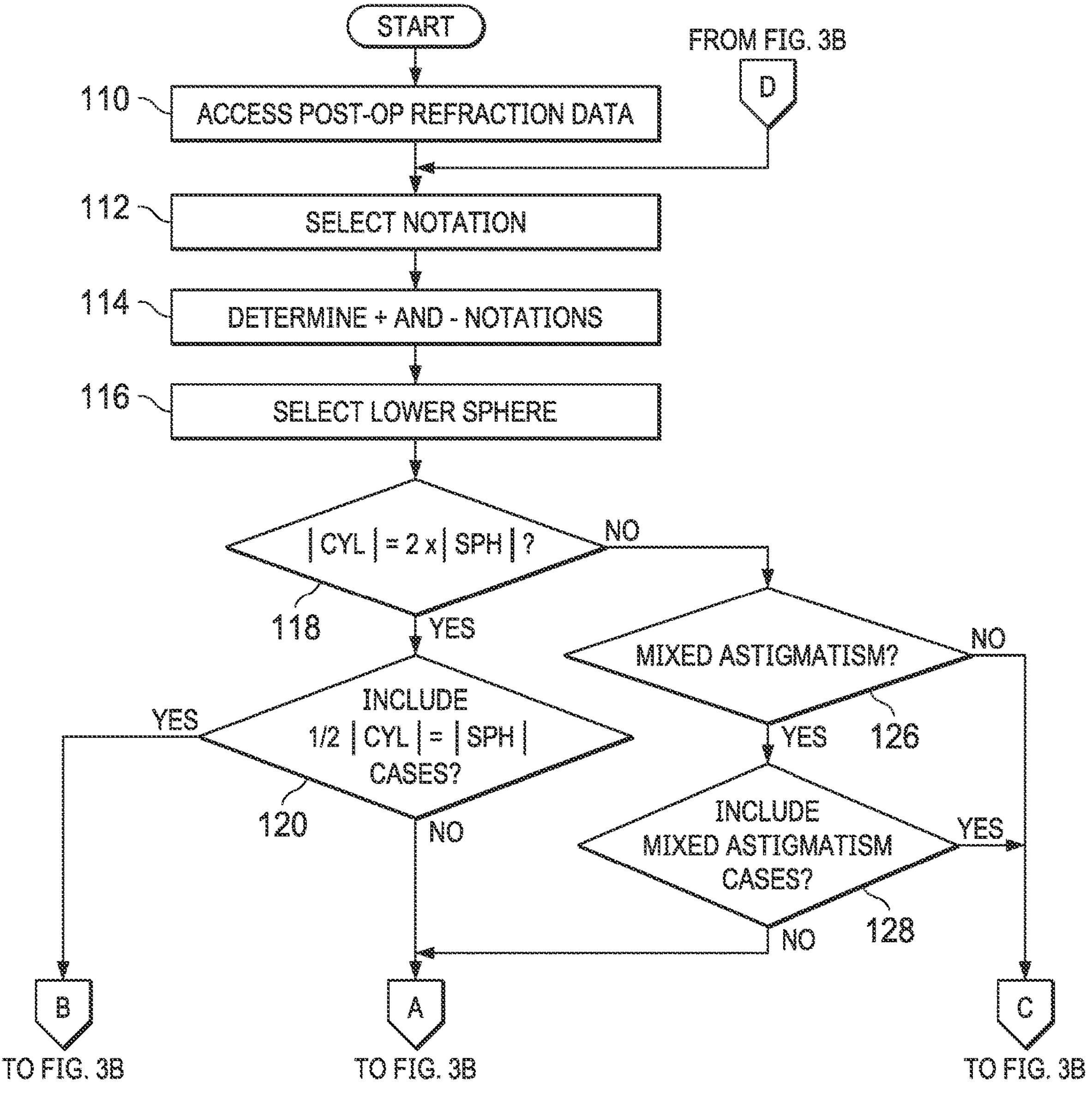
FIGS. 3A and 3B illustrate an example of a method for generating an ophthalmic nomogram for refractive treatment of an eye that may be performed by the system of FIG. 1, according to certain embodiments.
Figure 3B:
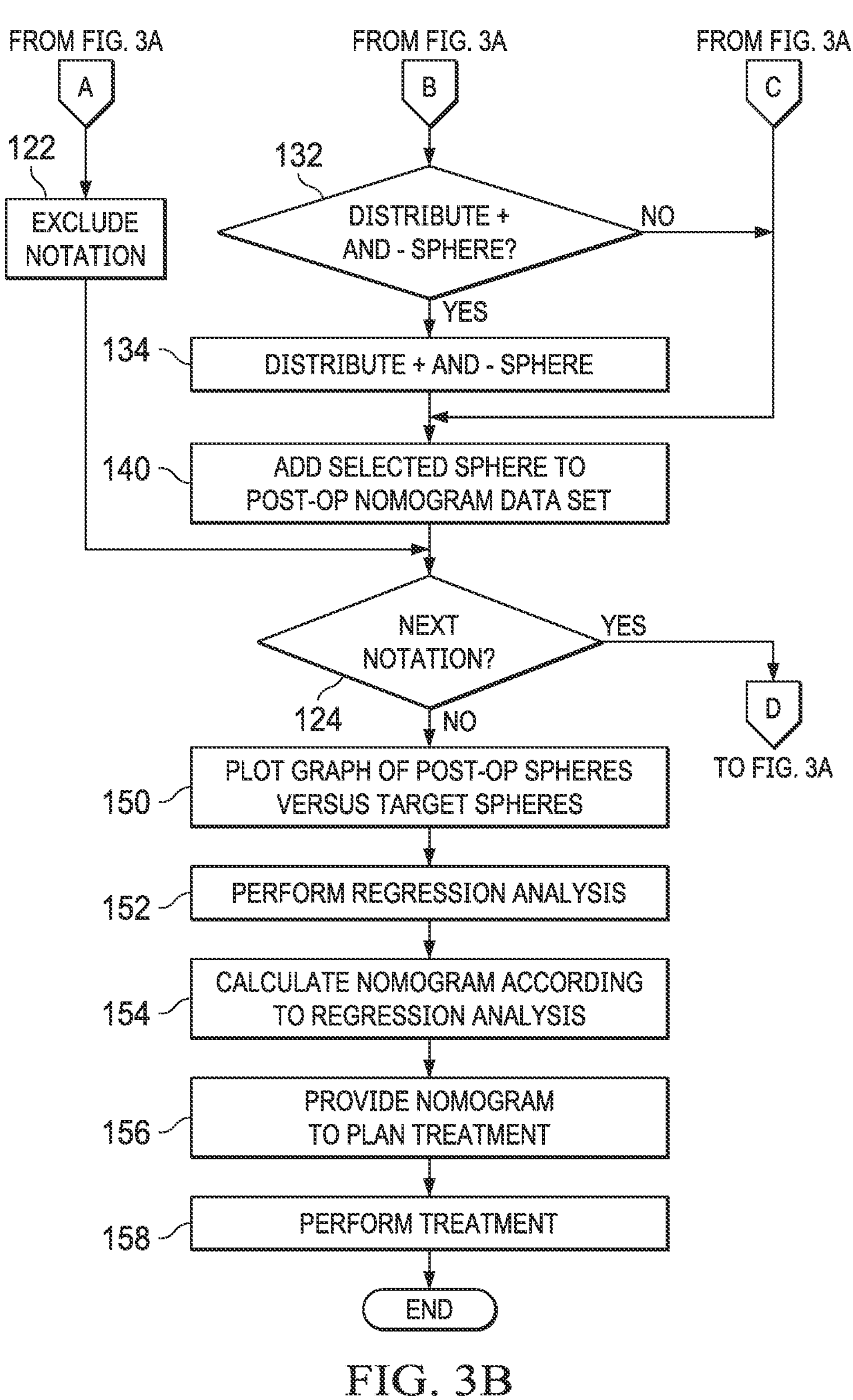
Figure 4:
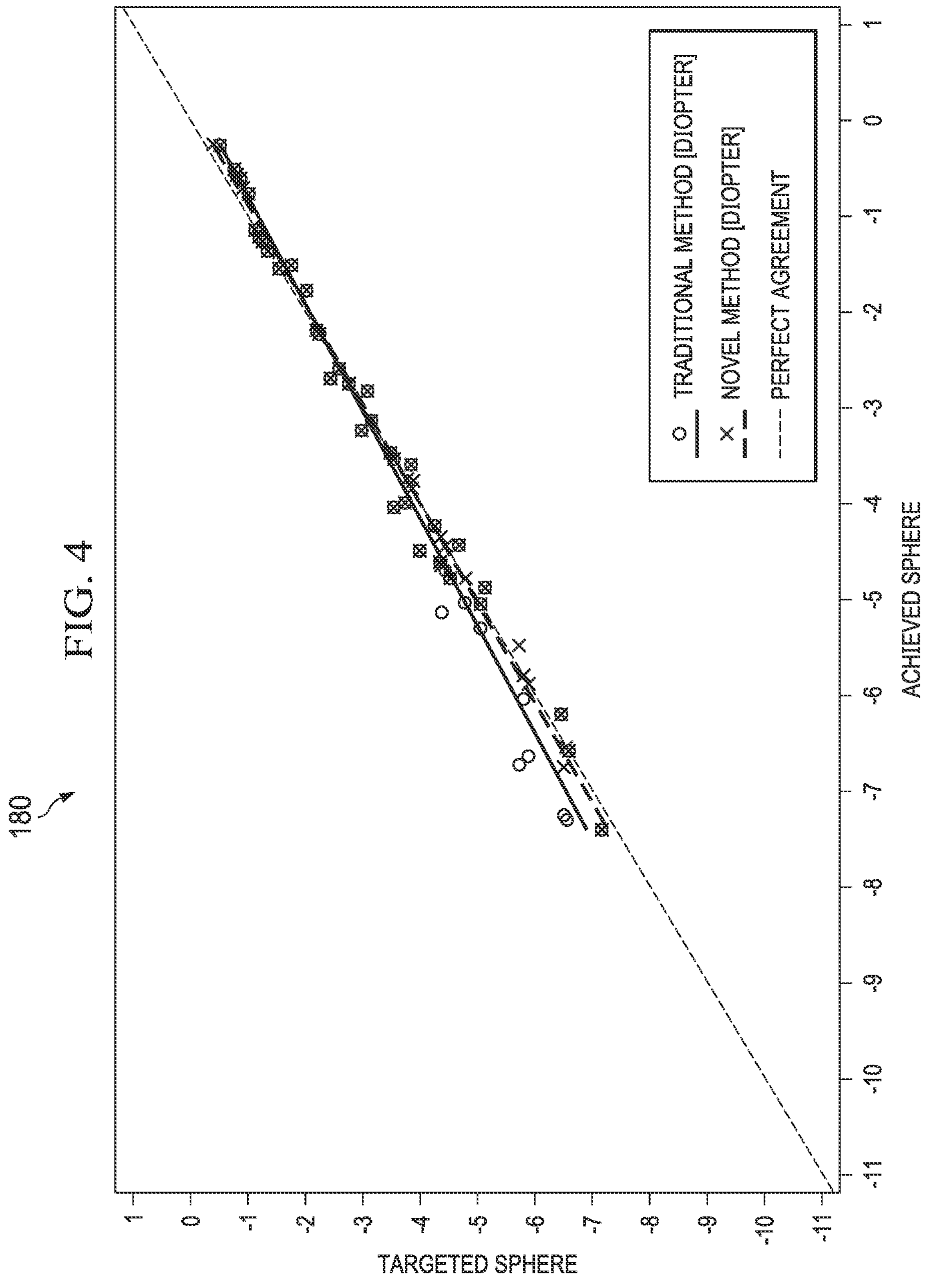
FIG. 4 illustrates an example of a graph of post-operation spheres versus their associated target spheres and lines of best fit for two data sets.

FIGS. 3A, 3B, and 4 illustrate an example of a method for generating an ophthalmic nomogram for ophthalmic treatment of an eye that may be performed by system 10 of FIG. 1, according to certain embodiments. The method analyzes astigmatism cases to reduce the effect of the spherical components of astigmatism notation. In certain embodiments, a user may select whether to implement the method. In other embodiments, the computer may be programmed to automatically implement the method.

In the example, a computer of system 10 performs at least some steps of the method. The computer stores a computer program and post-operation refraction data for generating the ophthalmic nomogram. The post-operation refraction data include refractive notations describing target corrections and their associated post-operation corrections. The refractive notations comprise a sphere and cylinder. The logic executes the computer program to select spheres of the post-operation corrections to create a nomogram data set used to generate the ophthalmic nomogram. The spheres are selected to reduce the spurious effects of the user's preference for plus or minus notation and the mixed astigmatism misdescription of spherical components.

The method starts at step 110, where the computer accesses the post-operation refraction data. Steps 112 to 140 are performed for each refractive notation to yield the nomogram data set. The computer selects a notation from the post-operation refraction data at step 112. The computer determines a plus or minus notation at step 114. If the notation is expressed as a plus notation, the corresponding minus notation is determined. If the notation is expressed as a minus notation, the corresponding plus notation is determined. The computer identifies whether the plus notation or the minus notation has a lower absolute sphere, and selects the lower absolute sphere as a candidate sphere at step 116.

The absolute cylinder $|cyl|$ may be equal to twice the absolute sphere $|sph|$, or $|cyl|=2\times|sph|$, at step 118. If a user has a preferred cylinder notation, then these cases can skew the results. If $|cyl|=2\times|sph|$, the method proceeds to step 120, where $\frac{1}{2}\,|cyl|=|sph|$ cases may be included or excluded. In certain embodiments, a user may select whether to include or exclude such cases from the nomogram data set. In other embodiments, the selection may be predetermined by settings of the computer program. If $\frac{1}{2}\,|cyl|=|sph|$ cases are to be included, the method proceeds to step 132. If $\frac{1}{2}\,|cyl|=|sph|$ cases are to be excluded, the method proceeds to step 122, where the notation is excluded. The method then proceeds to step 124, where there may be a next notation of the post-operation refraction data. If $|cyl|$ is not equal to $2\times|sph|$, the method proceeds to step 126.

The case may be a mixed astigmatism at step 126. A case can be identified as a mixed astigmatism if, for + and − notation, the absolute cylinder is greater than the absolute sphere i.e., $|cyl|>|sph|$, and no sphere of any notation is 0 D. 0 D identifies a pure astigmatism, either myopic or hyperopic. If the notation describes a mixed astigmatism, the method proceeds to step 128, where mixed astigmatism cases may be included or may be excluded to reduce the spurious effects of the astigmatism sphere component. In certain embodiments, a user may select whether to include or exclude the mixed astigmatism case. In other embodiments, the selection may be predetermined by settings of the computer program. If the mixed astigmatism is to be included at step 128, the method proceeds to step 140. If the mixed astigmatism is to be excluded at step 128, the method proceeds to step 122, where the mixed astigmatism notation is excluded.

TABLE 1 lists examples of cases for steps 110 through 128 of the method.

TABLE 1

| Step | Case 1 | Case 2 | Case 3 | Case 4 |
|---|---|---|---|---|
| 110: Access post-op refraction data | +0.25 −0.50 0° | +1.00 −1.00 0° | +0.50 −0.75 0° | −0.50 −0.50 0° |
| 114: Determine +/− notations | +0.25 −0.50 0° −0.25 +0.50 90° | +1.00 −1.00 0° 0.00 +1.00 90° | +0.50 −0.75 0° −0.25 +0.75 90° | −0.50 −0.50 0° −1.00 +0.50 −90° |
| 116: Select lower sphere | −0.25 +0.50 90° | 0.00 +1.00 90° | −0.25 +0.75 90° | −0.50 −0.50 0° |
| 118: $\lvert cyl\rvert = 2\times\lvert sph\rvert$? | Yes, go to step 120. | No, go to step 126. | No, go to step 126. | No, go to step 126. |
| 120: Include $\frac{1}{2}\,\lvert cyl\rvert = \lvert sph\rvert$? | If yes, go to step 132. If no, go to step 122. | Step skipped. | Step skipped. | Step skipped. |
| 126: Mixed astigmatism? | Step skipped. | No, go to step 140. | Yes, go to step 128. | No, go to step 140. |
| 128: Include mixed astigmatism? | Step skipped. | Step skipped | If yes, go to step 140. If no, go to step 122. | Step skipped. |

The computer may perform a distribution procedure to reduce the effect that $|cyl|=2\times|sph|$ cases have on the nomogram at step 132. In certain embodiments, a user may select whether to perform the distribution procedure. In other embodiments, the selection may be predetermined by settings of the computer program. If the distribution procedure is to be performed at step 132, the method proceeds to step 134, where the computer performs any suitable distribution procedure. For example, the plus or minus notation from which the sphere is selected may alternate at each iteration, where a new iteration starts from step 112 when a new notation is selected. If the sphere of the previous iteration was from the minus notation, the sphere of the plus notation is selected. If the sphere of the previous iteration was from the plus notation, the sphere of the minus notation is selected. As another example, the computer may randomly select the sphere of either the plus notation or the minus notation. The selected sphere is added to the nomogram data set at step 140. If a distribution procedure is not to be performed at step 132, the method proceeds to step 140, where the candidate sphere is designated as a selected sphere and added to the nomogram data set.

If the notation does not describe an astigmatism at step 126, the sphere from the notation with the lowest absolute sphere is added to the nomogram data set at step 140. After adding a sphere to the nomograph data set at step 140, the method proceeds to step 124, where there may be a next notation of the post-operation data set of target corrections and their associated post-operation corrections. If there is a next notation, the method returns to step 112 to select the next notation. If there is no next notation, the method had completed filling the nomograph data set with the selected spheres. The method proceeds to step 150.

Steps 150 to 154 are performed to create a graph and calculate the ophthalmic nomogram from the selected spheres. The computer plots the post-operation spheres versus target spheres at step 150. In certain embodiments, for each post-operation sphere of the nomograph data set, the computer identifies the target sphere associated with the post-operation sphere. The computer then creates a graph of the post-operation spheres versus the associated target spheres.

The computer performs a regression analysis of the spheres at step 152 to determine a line that describes the relationship between post-operation and target spheres, e.g., a line of best fit. Any suitable regression analysis (e.g., least squares) may be performed in any suitable manner. For example, regression may be performed for the entire diopter range of the data, e.g., from 0 to −8 of graph 180. As another example, the diopter range may be segmented, and regression may be performed for each segment, e.g., separate regression may be performed for 0 to −2, −2 to −4, −4 to −6, and −6 to −8.

FIG. 4 illustrates an example of a graph 180 of post-operation achieved spheres versus their associated target spheres and lines of best fit for two data sets. In the example, the Perfect Agreement line represents post-operation spheres that match their target spheres. The Traditional Method line is generated from a data set (represented by circles) selected according to a method that does not reduce the spurious effects of astigmatism spherical components. The Novel Method line is generated from a data set (represented by pluses) selected according to the novel methods described herein that reduce the spurious effects. As graph 180 shows, the Novel Method line is closer to the Perfect Agreement line than is the Traditional Method line. This indicates that reducing the effects of astigmatism notation is likely reducing a spurious effect.

The computer can create the graph from all elements of or any suitable subset of the nomogram data set. The subset, which may be selected by the user, may be selected according to any suitable factor, such as a particular class of patients. For example, the subset may be associated with: patients that have been refracted in particular manner, e.g., objective, subjective, cyclo-objective, and/or cyclo-subjective; patients within a particular age range; or patients that require correction within a particular diopter range.

Returning to the flowchart of FIGS. 3A and 3B, the computer generates the nomogram according to the regression analysis at step 154. In certain nomograms, the nomogram may describe the relationship between post-operation and target spheres, as, e.g., the line of best fit. The nomogram can indicate adjustments that yield particular actual post-operation corrections. For example, graph 180 indicates to achieve a −7 diopter post-operation correction, the laser device should be programmed to perform a −6.95 diopter correction. As another example, to achieve a −1 diopter post-operation correction, the laser device should be programmed to perform a 1.05 diopter correction.

The computer provides the nomogram to plan the refractive treatment at step 156. In certain embodiments, the computer provides the nomogram to a treatment planning program, so the computer and/or surgeon can plan the refractive treatment for the eye according to the ophthalmic nomogram. For example, the planning program may automatically incorporate adjustments indicated by the nomogram into treatment planning. As another example, the planning program may make the nomogram available to a user, so they may decide how to make the adjustments. The computer may then generate a laser shot list that yields the planned refractive treatment.

The laser device performs the refractive treatment step 158. In certain embodiments, the computer may instruct the laser device to perform the refractive treatment planned according to the ophthalmic nomogram. In this way, the laser device utilizes the nomogram to execute the refractive treatment. The computer may instruct the laser device by sending the laser shot list for the treatment, and the laser device performs the treatment by directing laser pulses toward the eye according to the laser shot list. The method then ends.

A component (such as computer 30) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface is a type of interface that a user can utilize to communicate with (e.g., send input to and/or receive output from) a computer. Examples of user interfaces include a display, Graphical User Interface (GUI), touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by an electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server or cloud-based storage), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art. A computer may be part of a system, a cloud server, or an artificial intelligence environment.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. A system for generating an ophthalmic nomogram for treating an eye, comprising:

a computer comprising:

a memory configured to store a computer program and post-operation refraction data for generating the ophthalmic nomogram, the post-operation refraction data comprising a plurality of notations, each notation comprising a sphere and a cylinder, each notation describing a post-operation correction associated with a target correction, the target correction having a target sphere; and logic configured to execute the computer program to create a nomogram data set comprising a plurality of selected spheres, the logic executing the computer program configured to:

perform the following for each notation of the plurality of notations to yield the plurality of selected spheres:

when the notation is expressed as a plus notation, determine a minus notation corresponding to the plus notation;

when the notation is expressed as a minus notation, determine a plus notation corresponding to the minus notation;

identify whether the plus notation or the minus notation has a lower absolute sphere;

designate the lower absolute sphere of the identified notation as a candidate sphere; and determine whether to designate the candidate sphere as a selected sphere; and calculate the ophthalmic nomogram from the plurality of selected spheres.

2. The system of claim 1, the logic configured to determine whether to designate the candidate sphere as a selected sphere by:

if an absolute cylinder of the notation is equal to two times an absolute sphere of the notation, determining whether to include or exclude the candidate sphere from the plurality of selected spheres.

3. The system of claim 1, the logic configured to determine whether to designate the candidate sphere as a selected sphere by:

if an absolute cylinder of the notation is not equal to two times an absolute sphere of the notation, determining whether the notation describes a mixed astigmatism.

4. The system of claim 1, the logic configured to determine whether to designate the candidate sphere as a selected sphere by:

if the notation describes a mixed astigmatism, determining whether to include or exclude the candidate sphere.

5. The system of claim 1, the logic configured to:

determine that an absolute cylinder of the notation is equal to two times an absolute sphere of the notation; and perform a distribution procedure to distribute plus notations and minus notations of the plurality of selected spheres.

6. The system of claim 5, the logic configured to performing the distribution procedure by:

if a sphere of a previous iteration was from the minus notation, selecting the sphere of the plus notation; and if the sphere of the previous iteration was from the plus notation, selecting the sphere of the minus notation.

7. The system of claim 6, the logic configured to performing the distribution procedure by:

randomly selecting the sphere of either the plus notation or the minus notation as the selected sphere.

8. The system of claim 1, the logic configured to calculate the ophthalmic nomogram from the plurality of selected spheres by:

performing the following for each selected sphere of the nomogram data set:

determining a post-operation correction corresponding to a selected sphere; and identifying the target sphere of the target correction associated with the post-operation correction; and creating a graph of the post-operation spheres versus the target spheres.

9. The system of claim 8, the logic configured to create the graph of the post-operation spheres versus the target spheres by:

performing a regression analysis of the post-operation spheres versus the target spheres in order to determine a line that describes a relationship between the post-operation spheres and the target spheres.

10. The system of claim 8, the logic configured to create the graph of the post-operation spheres versus the target spheres by:

performing a first regression analysis for a first diopter range of the post-operation spheres versus the target spheres to determine a first line that describes a relationship between the post-operation spheres and the target spheres in the first diopter range; and performing a second regression analysis for a second diopter range of the post-operation spheres versus the target spheres to determine a second line that describes a relationship between the post-operation spheres and the target spheres in the second diopter range.

11. The system of claim 1, the logic configured to calculate the ophthalmic nomogram from the plurality of selected spheres by:

identifying a subset of the plurality of selected spheres corresponding to a class of patients; and calculating the ophthalmic nomogram from the subset of the plurality of selected spheres.

12. The system of claim 1, the logic further configured to:

plan a treatment for the eye according to the ophthalmic nomogram.

13. The system of claim 12, further comprising:

a laser device configured to perform the treatment for the eye.

14. A method for generating an ophthalmic nomogram for treating an eye, comprising:

storing, by a computer, a computer program and post-operation refraction data for generating the ophthalmic nomogram, the post-operation refraction data comprising a plurality of notations, each notation comprising a sphere and a cylinder, each notation describing a post-operation correction associated with a target correction, the target correction having a target sphere;

executing, by the computer, the computer program to create a nomogram data set comprising a plurality of selected spheres, the computer executing the computer program comprising:

performing the following for each notation of the plurality of notations to yield the plurality of selected spheres:

when the notation is expressed as a plus notation, determining a minus notation corresponding to the plus notation;

when the notation is expressed as a minus notation, determining a plus notation corresponding to the minus notation;

identifying whether the plus notation or the minus notation has a lower absolute sphere;

designating the lower absolute sphere of the identified notation as a candidate sphere; and determining whether to designate the candidate sphere as a selected sphere; and calculating the ophthalmic nomogram from the plurality of selected spheres.

15. The method of claim 14, the determining whether to designate the candidate sphere as a selected sphere further comprising:

if an absolute cylinder of the notation is equal to two times an absolute sphere of the notation, determining whether to include or exclude the candidate sphere from the plurality of selected spheres.

16. The method of claim 14, the determining whether to designate the candidate sphere as a selected sphere further comprising:

if an absolute cylinder of the notation is not equal to two times an absolute sphere of the notation, determining whether the notation describes a mixed astigmatism.

17. The method of claim 14, the determining whether to designate the candidate sphere as a selected sphere further comprising:

if the notation describes a mixed astigmatism, determining whether to include or exclude the candidate sphere.

18. The method of claim 14, further comprising:

determining that an absolute cylinder of the notation is equal to two times an absolute sphere of the notation; and performing a distribution procedure to distribute plus notations and minus notations of the plurality of selected spheres.

19. The method of claim 14, the calculating the ophthalmic nomogram from the plurality of selected spheres further comprising:

performing the following for each selected sphere of the nomogram data set:

determining a post-operation correction corresponding to a selected sphere; and identifying the target sphere of the target correction associated with the post-operation correction; and creating a graph of the post-operation spheres versus the target spheres.

20. The method of claim 14, further comprising:

planning a treatment for the eye according to the ophthalmic nomogram.

21. A system for generating an ophthalmic nomogram for treating an eye, comprising:

a computer comprising: a memory configured to store a computer program and post-operation refraction data for generating the ophthalmic nomogram, the post-operation refraction data comprising a plurality of notations, each notation comprising a sphere and a cylinder, each notation describing a post-operation correction associated with a target correction, the target correction having a target sphere; and logic configured to execute the computer program to create a nomogram data set comprising a plurality of selected spheres, the logic executing the computer program configured to:

perform the following for each notation of the plurality of notations to yield the plurality of selected spheres:

when the notation is expressed as a plus notation, determine a minus notation corresponding to the plus notation;

when the notation is expressed as a minus notation, determine a plus notation corresponding to the minus notation;

identify whether the plus notation or the minus notation has a lower absolute sphere;

designate the lower absolute sphere of the identified notation as a candidate sphere; and determine whether to designate the candidate sphere as a selected sphere by:

when an absolute cylinder of the notation is equal to two times an absolute sphere of the notation, determining whether to include or exclude the candidate sphere from the plurality of selected spheres;

when an absolute cylinder of the notation is not equal to two times an absolute sphere of the notation, determining whether the notation describes a mixed astigmatism; and when the notation describes a mixed astigmatism, determining whether to include or exclude the candidate sphere;

determine that an absolute cylinder of the notation is equal to two times an absolute sphere of the notation; and perform a distribution procedure to distribute plus notations and minus notations of the plurality of selected spheres by:

when a sphere of a previous iteration was from the minus notation, selecting the sphere of the plus notation, and if the sphere of the previous iteration was from the plus notation, selecting the sphere of the minus notation; or randomly selecting the sphere of either the plus notation or the minus notation as the selected sphere;

calculate the ophthalmic nomogram from the plurality of selected spheres by: performing the following for each selected sphere of the nomogram data set:

determining a post-operation correction corresponding to a selected sphere; and identifying the target sphere of the target correction associated with the post-operation correction;

creating a graph of the post-operation spheres versus the target spheres by: performing a regression analysis of the post-operation spheres versus the target spheres in order to determine a line that describes a relationship between the post-operation spheres and the target spheres; and performing a first regression analysis for a first diopter range of the post-operation spheres versus the target spheres to determine a first line that describes a relationship between the post-operation spheres and the target spheres in the first diopter range, and performing a second regression analysis for a second diopter range of the post-operation spheres versus the target spheres to determine a second line that describes a relationship between the post-operation spheres and the target spheres in the second diopter range; and identifying a subset of the plurality of selected spheres corresponding to a class of patients, and calculating the ophthalmic nomogram from the subset of the plurality of selected spheres; and plan a treatment for the eye according to the ophthalmic nomogram; and a laser device configured to perform the treatment for the eye.

* * * * *